United States Patent [19]

Hargis et al.

[11] 4,370,507

[45] Jan. 25, 1983

[54] ETHANOL FROM METHANOL AND SYNTHESIS GAS

[75] Inventors: Duane C. Hargis, Pleasant Ridge; Michael Dubeck, Birmingham, both of Mich.

[73] Assignee: Ethyl Corporation, Richmond, Va.

[21] Appl. No.: 338,088

[22] Filed: Jan. 8, 1982

Related U.S. Application Data

[62] Division of Ser. No. 186,217, Sep. 11, 1980.

[51] Int. Cl.³ ............................................. C07C 29/00
[52] U.S. Cl. ................................................... 568/902
[58] Field of Search ........................................ 568/902

[56] References Cited

U.S. PATENT DOCUMENTS

| | | | |
|---|---|---|---|
| 2,623,906 | 12/1952 | Greshaw | 568/902 |
| 3,248,432 | 4/1968 | Riley et al. | 568/902 |
| 3,285,948 | 11/1966 | Butter | 568/902 |
| 4,013,700 | 3/1977 | Cawse | 252/431 R |
| 4,133,966 | 1/1979 | Pretzer | 568/902 |
| 4,235,801 | 11/1980 | Bhasia | 518/716 |
| 4,301,312 | 11/1981 | Feder et al. | 568/902 |
| 4,309,314 | 1/1982 | Hargis et al. | 568/902 |

*Primary Examiner*—Joseph E. Evans
*Attorney, Agent, or Firm*—Donald L. Johnson; Joseph D. Odenweller; Teresa M. Stanek

[57] ABSTRACT

A process for selectively preparing ethanol by contacting methanol, hydrogen and carbon monoxide with a solid catalyst comprising rhodium and iron in the reduced state deposited on a support of alumina impregnated with a promoter amount of a heterocyclic amine at reaction conditions correlated so as to favor the formation of a substantial proportion of ethanol.

6 Claims, No Drawings

ETHANOL FROM METHANOL AND SYNTHESIS GAS

This application is a division of application Ser. No. 186,217, filed Sept. 11, 1980.

BACKGROUND OF THE INVENTION

This invention concerns the selective preparation of ethanol from methanol and synthesis gas. More particularly, the invention concerns the reaction of methanol and synthesis gas under heterogenous reaction conditions in the presence of a catalyst of rhodium and iron on an alumina support containing a promoter amount of a heterocyclic amine to produce ethanol.

The reaction of methanol with hydrogen and carbon monoxide to produce ethanol and other oxygen-containing organic compounds is known and disclosed in the prior art. For example, U.S. Pat. No. 4,133,966 entitled SELECTIVE FORMATION OF ETHANOL FROM METHANOL, HYDROGEN AND CARBON MONOXIDE discloses a process for the selective formation of ethanol which comprises contacting methanol, hydrogen and carbon monoxide with a catalyst system comprising cobalt acetylacetonate, a tertiary organo Group V A compound of the Periodic Table, a first promoter comprising an iodine compound and a second promoter compound comprising a ruthenium compound.

U.S. Pat. No. 3,285,948 entitled HALIDES OF RUTHENIUM AND OSMIUM IN CONJUNCTION WITH COBALT AND IODINE IN THE PRODUCTION OF ETHANOL FROM METHANOL, issued to Butter on Nov. 15, 1966, teaches a method for producing alcohols in which any source of cobalt soluble in the reaction medium which will yield a cobalt carbonyl or hydrogen cobalt carbonyl under the reaction conditions can be used. In addition, an iodine promoter is employed, for example $I_2$, or alkali metal iodines. A secondary promoter is also employed, i.e., ruthenium halide or osmium halide. High selectivity is described as better when the secondary promoter is used in combination with the primary promoter and other reactants.

U.S. Pat. No. 4,013,700, entitled CATALYTIC PROCESS FOR POLYHYDRIC ALCOHOLS AND DERIVATIVES, issued to Cawse on Mar. 22, 1977, discloses a process for the preparation of polyhydric alcohols, their ether and ester derivatives, and oligomers of such alcohols. In particular, these alcohols and their derivatives are produced by reacting the oxides of carbon and hydrogen in the presence of a quaternary phosphonium cation and a rhodium carbonyl complex at elevated temperature and pressure.

Another process is set forth in U.S. Pat. No. 3,248,432, entitled PROCESS FOR THE PRODUCTION OF ETHYL ALCOHOL, issued to Riley et al on Apr. 26, 1966, which relates to a process for the production of ethyl alcohol by the interaction of methanol, carbon monoxide and hydrogen at elevated temperature and pressure in the presence of a cobalt catalyst and an iodine promoter. Examples of suitable cobalt sources are described as any water-soluble source of cobalt, for example, the cobalt carbonyls, the lower salts of alkanoate cobalt, such as cobalt acetate, cobalt formate, cobalt propionate, and the like.

U.S. Pat. No. 2,623,906, entitled PREPARATION OF ORGANIC HYDROXY-CONTAINING COMPOUNDS BY REACTING ALCOHOLS WITH CARBON MONOXIDE AND HYDROGEN, issued to Greshaw on June 16, 1948, relates to a procedure for synthesizing mono and poly functional oxygen-containing organic compounds by the reaction of alcohols, carbon monoxide and hydrogen. Catalysts described as suitable for use include various cobalt compounds, for example, cobalt carbonyl, cobalt carbonyl hydride, metallic cobalt, and organic and inorganic cobalt salts.

Dutch Pat. No. 760,6138 entitled PROCESS FOR THE FORMATION OF ETHANOL FROM METHANOL AND SYNTHESIS GAS, issued to Shell International Research on June 8, 1976, relates to a process for producing alcohols which utilizes any soluble cobalt source which can generate a cobalt carbonyl or hydrocarbonyl by reaction with the synthesis gas. For example, sources of cobalt suitable for use are cobalt iodide or cobalt metal from which ions can be generated in situ. Organic salts of cobalt such as cobalt acetate, formate, or propionate are described as especially good sources, an iodide or bromide promoter is also utilized. In addition, the use of a tertiary phosphine is described as affording improved selectivity to the formation of alcohols.

U.S. application Ser. No. 437,141 filed Jan. 28, 1974, now abandoned, discloses a process for manufacturing acetic acid, its lower alkyl esters, ethanol and lower alkyl aldehydes by contacting a reaction mixture of an oxide of carbon and hydrogen with a solid metal catalyst from the group of rhodium, ruthenium, cobalt, osmium, iridium and platinum. In one embodiment disclosed therein, methanol is co-fed with hydrogen and carbon monoxide over a supported rhodium catalyst with the reported result that productivities of the process were improved with the addition of methanol to the fed gas.

U.S. application Ser. No. 541,660 filed Jan. 16, 1975, now abandoned, discloses a process for the selective preparation of ethanol by continuously contacting a synthesis gas reaction mixture containing hydrogen and carbon monoxide with a catalyst of rhodium and iron dispersed on a particulate support.

U.S. application Ser. No. 153,610 filed May 27, 1980, now U.S. Pat. No. 4,309,314 entitled CATALYTIC PROCESS FOR THE SELECTIVE FORMATION OF ETHANOL FROM METHANOL AND SYNTHESIS GAS discloses a process for making ethanol and methyl acetate by contacting methanol, hydrogen and carbon monoxide with a catalyst of rhodium and iron deposited on a support of alumina containing a minor amount of an alkaline metal.

So far as applicant is aware, however, no process is provided for selectively preparing ethanol by contacting a mixture of methanol, carbon monoxide and hydrogen with a heterogenous catalyst comprising rhodium and iron supported on an alumina support containing a heterocyclic amine. Unexpectedly, applicant has discovered that large amounts of ethanol can be produced by contacting such a gaseous reaction mixture with the catalyst composition disclosed herein.

SUMMARY OF THE INVENTION

Briefly, in accordance with the invention, a process is provided for the reaction of methanol, carbon monoxide and hydrogen to produce ethanol by passing a mixture of methanol, carbon monoxide and hydrogen over a solid catalyst of rhodium in combination with iron deposited on an alumina support impregnated with a heterocyclic amine, preferably pyridine, under suitable reaction conditions.

DESCRIPTION OF THE PREFERRED EMBODIMENT

Thus, one embodiment of the present invention is a process for selectively producing ethanol which comprises reacting methanol with carbon monoxide and hydrogen in the presence of a heterogenous catalyst comprising rhodium and iron in the reduced state deposited on a support of alumina impregnated with a promoter amount of a heterocyclic amine at reaction conditions correlated so as to favor the formation of a substantial proportion of ethanol.

The catalyst used in the practice of this invention is also believed novel and that its constituents differ from those of the prior art. Thus, another embodiment of the present invention is a catalyst for selectively converting methanol, carbon monoxide and hydrogen to ethanol, said catalyst comprising rhodium and iron in the reduced state deposited on a support of alumina impregnated with a promoter amount of a heterocyclic amine.

PROCESS DISCUSSION

The reaction is conducted at more or less conventional reactive conditions of temperature, pressure, gas composition, and space velocity so that conventional technology and equipment may be used. Overall, the reaction is conducted at reactive conditions of temperature, pressure, gas composition and space velocity which are correlated to achieve optimal selectivity for ethanol. The reaction efficiency, or selectivity, to ethanol is invariably in excess of 40% and is often between 60% and 70% excluding carbon dioxide and dimethyl ether as products. Selectivity is defined herein as the percentage of carbon atoms converted from carbon monoxide and methanol to a specified compound or compounds other than carbon dioxide.

The reaction is exothermic with the thermodynamic equilibra and the kinetic reaction rates being governed by the reaction temperature. In general, the temperature can range from about 225° C. to about 275° C. A preferred temperature is about 250° C.

The reaction zone pressure is desirably within the range of about 50 psig to about 250 psig, with a pressure of approximately 220 psig being preferred.

The ratio of hydrogen to carbon monoxide in the synthesis gas may vary somewhat. Normally, the mole ratio of hydrogen to carbon monoxide is within the range of about 2:1 to 1:2. Preferably, the mole ratio of hydrogen to carbon monoxide is about 1:1. Methanol is added to the synthesis gas prior to introducing the gaseous reactant mixture into the reaction zone. Typically, a mole ratio of methanol to carbon monoxide of approximately 1:1 is used in the practice of the present process.

Conversion is conveniently achieved by employing a high space velocity correlated with other reaction variables (e.g. temperature, pressure, gas composition, catalyst, etc.). Space velocities of from about 800 to about 2000 gas hourly space velocities (volumes of reactant gas at 0° C. and 760 mm mercury pressure, per volume of catalyst per hour) are generally employed. A preferred gas hourly space velocity is approximately 1200 GHSV.

THE CATALYST

The rhodium-iron-heterocyclic amine promoted catalyst of the present invention is rhodium provided in combination with iron on a suitable alumina support which has been impregnated with a heterocyclic amine.

Heterocyclic amines which are useful in the present process are the six-membered aromatic heterocycles which include pyridine and substituted pyridines. The substituted pyridines may have one or more substituents selected from hydrocarbyl, halogen, hydroxy, carbonyl, cyano, and the like. Illustrative examples of such substituted pyridines are 2-hydroxypyridine, 3-iodopyridine, 4-cyanopyridine, 4-acetylpyridine, 4(diphenyldimethyl)pyridine, 4,4'-trimethylenepyridine, isoquinoline, 2-ethyl-4-chloropyridine, 2,6-dimethyl-4-phenyl pyridine and the like. Pyridine, isoquinoline, and the $C_1$-$C_6$ alkyl substituted pyridines are preferred. These preferred alkyl substituted pyridines may be mono-, di-, or trialkyl substituted pyridines. Examples of these preferred alkyl substituted pyridines are 2-methylpyridine, 3,5-dimethylpyridine, 4-ethyl-3,5-dimethylpyridine, 4-butylpyridine, 3,4-diethylpyridine, 2-cyclohexylpyridine, 3-tert-butylpyridine, and the like. The alkyl substituted pyridines which have no substituent in the position ortho to the nitrogen atom in the pyridine ring are more preferred. Pyridine is most preferred. Catalyst preparation is typically effected by depositing rhodium and iron onto a high surface area alumina support and then impregnating the support with the amine aforedescribed.

In general, suitable support materials may include alpha alumina, beta alumina, gamma or eta alumina, alumino-silicates and magnesium silicates. Gamma alumina is the preferred catalyst support.

The rhodium and iron may be deposited onto the base or support by any of the techniques commonly used for catalyst impregnation, as for example, impregnation from an organic or inorganic solution, precipitation, etc. Conveniently, a solution of a heat decomposable inorganic or organic rhodium compound and an iron compound is appropriately contacted with the support material and the support is then dried and heated, the latter advantageously under reducing conditions, to form a finely dispersed rhodium-iron containing catalyst. These materials may be deposited concurrently or sequentially. Illustrative of water-soluble compounds are the chloride and nitrate salts of rhodium and iron. In preparing the catalyst composition, the support material is contacted with just enough solution of rhodium and iron compounds to wet the support so that little or no excess solution is used. This technique, which insures that the desired concentration of rhodium and iron will be incorporated into the catalyst composition, is known in the art and is referred to as the incipient wetness technique. After impregnating the support material, the catalyst is subjected to drying conditions to lower the water content of the resultant composition to the lowest possible level. In a typical drying procedure, the impregnated support is slowly heated from room temperature up to a temperature of approximately 100° C. and is maintained at this temperature for at least one hour, preferably from 1 to 24 hours, until substantially all of the water is removed from the composition. The dried composition is then reduced with hydrogen. It has been found advantageous to reduce the catalyst composition by contacting the composition in a reduction zone with hydrogen at room temperature and then heating the catalyst reduction zone slowly from room temperature up to a temperature of about 300° C. to 400° C. Reduction is continued at this temperature for approximately 1 to 24 hours, preferably 7 to 8 hours, until both the rhodium and iron components are reduced to the zero valent state. It is not critical that reduction of the dried catalyst composition be initiated at room temperature. Alternatively, the dried catalyst can be placed in the reduction zone immediately after drying and reduction can commence at an elevated temperature, for example, 200° C., as illustrated in Example 1 below.

The alumina support onto which the rhodium and iron components of the catalyst composition have been deposited is then impregnated with an aqueous solution of a heterocyclic amine, such as pyridine, using the incipient wetness technique, aforedescribed. Typically, the rhodium-iron containing support is contacted with 3-5 milliliters of a solution of pyridine dissolved in distilled water in an amount sufficient to provide from about 0.1 to about 10.0 percent by weight, and preferably from about 2.0 to about 6.0 percent by weight, of pyridine on the catalyst. Following adsorption of the amine on the support, the impregnated support material is dried at room temperature for at least one hour, and preferably for at least 16 to 24 hours, to remove water from the composition. After drying, the composition is then reduced with hydrogen by contacting the composition in a reduction zone with hydrogen and slowly heating the reduction zone from room temperature up to approximately 300° C. The reduction zone is maintained at this temperature for approximately 1 to 24 hours in order to effect reduction of the final composition.

It is preferred that the catalyst contain from about 1.0 to about 10.0 weight percent rhodium and from about 1.0 to about 10.0 weight percent iron based on the total weight of the catalyst composition. The amount of amine in the composition should range from about 0.1 weight percent to about 10.0 weight percent based on the total weight of the composition. An especially effective catalyst composition has been found to comprise approximately 3.3 percent by weight rhodium metal and 3.4 percent by weight metallic iron on a gamma-alumina support impregnated with 4.2 percent by weight pyridine.

After the catalyst has been prepared, the bulk volume of the weighed catalyst is determined and the sample is placed in a test reactor (described below). The quantity of catalyst charged to the reactor is typically about 2.0 to 3.0 grams.

TEST REACTOR

The reactor used in the practice of the present invention is a stainless steel tube of 0.305 in. internal diameter, 0.375 in. outside wall diameter with a wall thickness of 0.035 in. The length is 14 inches and the reactor capacity is approximately 16.5 ml. The tube is packed with a catalyst prepared as described above supported on a glass wool support. Carbon monoxide and hydrogen are fed to the reactor in the desired mole ratio from 1750 psig headers. Approximately 2.0 to 3.0 grams of catalyst are placed in the reactor on the support. The reactor is then pressurized with hydrogen and the flow of carbon monoxide and hydrogen is adjusted to achieve the desired composition. During pressurization of the reactor, the reactor temperature and pressure are adjusted to reaction conditions. At least 5 to 6 hours are usually allowed for the reactor to come to a steady state before beginning to measure actual time of reaction. Methanol is then mixed with the carbon monoxide and hydrogen components of the gaseous reaction mixture in the desired mole ratio and the composite mixture is fed into the reaction zone of the reactor. The reaction is allowed to proceed and samples of liquid product are collected periodically by collecting the product containing gas through a cold water condenser at approximately 225 psig and then trapping the liquid product in a dry-ice acetone trap having a capacity of approximately 55 cc. The liquid product from the trap and the condenser are then combined to obtain a single liquid sample which is analyzed by gas chromatography. The non-condensable gases are metered through a wet-test meter to determine the volume of gas, and gas samples are collected to determine their composition.

The following example serves to provide specific illustrations of the present invention.

EXAMPLE 1

This example illustrates the promoter effect that a heterocyclic amine, such as pyridine, has on the production of ethanol from methanol and synthesis gas.

A solution was prepared by dissolving 1.7384 grams of rhodium trichloride, $RhCl_3.3H_2O$, (obtained commercially from Alfa Products, 152 Andover Street, Danvers, Maine 01923) and 8.7320 grams of ferric nitrate, $Fe(NO_3)_3.9H_2O$ (obtained from the J. T. Baker Chemical Company, Phillipsburg, N.J. 08865) in distilled water to a final volume of 50 milliliters. The solution was heated until lukewarm to dissolve all of the salts so that the solution appeared homogeneous. The resultant aqueous solution was used to impregnate 22.5 grams of gamma-alumina (1.2 mm) obtained from Rhone-Poulenc Industries, Division Chimic Fine, 30340 Usine, De Salindres by adding the solution to the gamma-alumina support in a 250 milliliter suction flask. The support was submerged in the solution over the weekend. The support and solution were then poured into a crystallizing dish and heated over a hot plate set on the "Low" position for about 5 hours. The impregnated support was then dried in an oven at 100° C. overnight. The composition was then placed in the tubular test reactor, aforedescribed, and reduced with hydrogen by flowing hydrogen over the composition for approximately 6 hours while slowly increasing the temperature in the reduction zone from 200° C. to about 400° C. The composition was then reduced overnight at approximately 400° C. The resultant composition was a gamma-alumina supported catalyst containing approximately 3.3 weight percent rhodium and approximately 3.4 weight percent iron. This catalyst is referred to hereinafter as Catalyst A.

A second catalyst was prepared containing a promoter amount of pyridine by impregnating 3.05 grams of the catalyst prepared as described above with 0.127 grams of pyridine dissolved in 3 milliliters of distilled water using the incipient wetness technique. This produced a catalyst composition containing approximately 3.3 weight percent rhodium, 3.4 weight percent iron and 4.2 weight percent pyridine. The composite composition was then dried at room temperature overnight. Following this, the composition was reduced in hydrogen at 300° C. for approximately 7 hours. This catalyst is referred to hereinafter as Catalyst B.

The catalysts, prepared as described above, were used in the following reactions to demonstrate the selectivity of the amine promoter for producing ethanol from methanol, carbon monoxide and hydrogen. The reactions were conducted in the tubular flow test reactor aforedescribed under the conditions designated in the Table below. The mole ratio of hydrogen to carbon monoxide in all reactions was approximately 1:1. In those reactions where methanol was co-fed as a reactant with hydrogen and carbon monoxide, the mole ratio of hydrogen to carbon monoxide to methanol was approximately 1:1:1. The reaction temperature was maintained at approximately 250° C. for all runs and the reaction pressure was held constant at approximately 220 psig for all runs. Runs 1 and 2 were separate runs. Runs 3-13 were continuous with product samples taken and analyzed at the times indicated.

moter of the invention in comparison with the rhodium-iron catalyst containing no promoter. As shown, the amine promoter produced significantly greater yields of ethanol at comparable reaction conditions. Ethanol yields with promoter varied from approximately 44% (Run No. 7) to 68% (Run No. 12) excluding carbon dioxide and dimethyl ether as products. In several of the runs, specifically, Runs No. 5, 9 and 12 ethanol yields exceeded 60%. The specific activity of the catalyst is represented by a "turnover number" which is defined as

TABLE 1

EFFECT OF AMINE PROMOTER ON CATALYST SYSTEM

| | Catalyst A | | | | Catalyst B | | | |
|---|---|---|---|---|---|---|---|---|
| Run No. | 1 | 2 | 3 | 4 | 5[a] | | 6 | 7 |
| $H_2/CO$ | 1.0 | 1.0 | 1.0 | 1.0 | 1.0 | | 1.0 | 1.0 |
| Temp °C. | 250 | 250 | 250 | 250 | 250 | | 250 | 250 |
| Pressure, psig | 220 | 220 | 220 | 220 | 220 | | 220 | 220 |
| CO, moles/hr | .134 | .134 | .134 | .134 | .134 | | .134 | .134 |
| MeOH, moles/hr | .176 | .114 | 0 | 0 | .125 | | .123 | .129 |
| GHSV | 1990 | 1710 | 1200 | 1200 | 1760 | | 1750 | 1780 |
| Time (hrs) from start of reaction | 2.2 | 2.8 7.3 | 15.8 6.5 | 44.8 6.3 | 46.9 10.8 | | 48.9 9.2 | 50.9 8.3 |
| C Conv, % | 5.7 | * | * | | * | | * | * |
| Product Distribution, C % | | | | | | | | |
| $CO_2$ | 5.2 | 6.2 | 5.4 | 6.6 | 8.1 | | 8.7 26.1 | 8.8 |
| $CH_4$ | 9.8 | 27.8 11.9 32.7 | 36.2 | 32.2 | 8.6 | 17.3 | 10.2 11.6 | 10.2 |
| $C_2-C_5$ HC | 3.2 | 9.1 2.3 6.3 | 11.5 | 9.2 | 3.8 | 7.7 | 4.6 | 4.7 |
| $Me_2O$ | 59.7 | 57.4 | .1 | .1 | 42.2 | | 52.2 | 53.7 |
| MeOH | | | 18.1 | 7.0 | | | | |
| EtOH | 14.1 | 40.2 14.9 40.9 | 16.9 | 34.4 | 31.1 | 62.7 | 18.9 48.3 | 16.2 |
| MeOAc | 6.5 | 18.4 5.2 14.4 | 1.2 | 1.5 | 3.5 | 7.0 | 3.7 9.5 | 4.6 |
| other oxygenates | 1.7 | 4.8 2.1 6.0 | 11.9 | 9.2 | 2.7 | 5.3 | 1.8 4.4 | 1.9 |
| Turnover No, umole/g-min | | | | | | | | |
| $CO_2$ | 5.01 | 6.09 | 2.57 | 3.02 | 12.3 | | 11.1 | 10.5 |
| $CH_4$ | 9.47 | 11.8 | 17.3 | 14.8 | 13.1 | | 13.1 | 12.1 |
| $C_2-C_5$ HC | 1.09 | .75 | 1.89 | 1.46 | 1.98 | | 1.98 | 1.88 |
| $Me_2O$ | 29.0 | 28.4 | .019 | .021 | 32.1 | | 33.1 | 32.0 |
| MeOH | | | 8.67 | 3.22 | | | | |
| EtOH | 6.86 | 7.36 | 4.05 | 7.94 | 23.7 | | 12.1 | 9.65 |
| MeOAc | 2.09 | 1.72 | .20 | .22 | 1.77 | | 1.59 | 1.84 |
| other oxygenates | .13 | .99 | 1.68 | 1.39 | 1.67 | | .91 | .82 |
| $H_2O$ | 106 | 78.0 | 16.7 | 30.1 | 2.39 | | 1.28 | 1.06 |

| | Catalyst B | | | | | | |
|---|---|---|---|---|---|---|---|
| Run No. | 8 | 9 | 10[b] | | 11 | 12 | 13 |
| $H_2/CO$ | 1.0 | 1.0 | 1.0 | | 1.0 | 1.0 | 1.0 |
| Temp °C. | 250 | 250 | 250 | | 250 | 250 | 250 |
| Pressure, psig | 220 | 220 | 220 | | 220 | 220 | 220 |
| CO, moles/hr | .134 | .134 | .134 | | .134 | .134 | .134 |
| MeOH, moles/hr | 0 | .124 | .115 | | 0 | .120 | .122 |
| GHSV | 1200 | 1750 | 1710 | | 1200 | 1740 | 1750 |
| Time (hrs) from start of reaction | 67.2 8.2 | 69.3 12.5 | 72.1 7.9 | | 88.1 7.4 | 90.6 | 92.9 8.1 |
| C Conv, % | | | | | | 11.2 | |
| Product Distribution, C % | * | | * | | * | * | |
| $CO_2$ | | 6.9 | 5.7 | | 11.8 | 7.3 6.0 | 8.1 |
| $CH_4$ | 27.2 | 33.6 | 6.7 11.4 | 9.7 | 25.3 32.9 | 7.9 14.1 | 8.5 20.7 |
| $C_2-C_5$ HC | 12.5 | 8.3 | 2.6 4.5 | 3.3 | 8.7 8.3 | 2.8 5.1 | 2.7 6.6 |
| $Me_2O$ | | .3 | 35.3 | | 49.8 | .2 38.1 | 51.1 |
| MeOH | | 26.4 | | | | 12.8 | |
| EtOH | 43.2 | 18.2 | 39.7 67.3 | 18.3 | 47.5 30.2 | 38.0 68.0 | 22.7 55.4 |
| MeOAc | 12.3 | 1.7 | 4.4 7.5 | 5.1 | 13.1 1.3 | 4.0 7.1 | 5.3 13.0 |
| other oxygenates | 4.8 | 4.7 | 5.6 4.4 | 2.0 | 5.4 6.9 | 3.2 5.8 | 1.8 4.2 |
| Turnover No, umole/g-min | | | | | | | |
| $CO_2$ | | 4.10 | 9.98 | | 12.6 | 3.94 9.29 | 9.19 |
| $CH_4$ | | 20.1 | 11.8 | | 10.4 | 17.7 12.3 | 9.60 |
| $C_2-C_5$ HC | | 1.74 | 1.57 | | 1.25 | 1.53 1.45 | 1.08 |
| $Me_2O$ | | .10 | 30.9 | | 26.7 | .053 29.7 | 29.0 |
| MeOH | | 15.8 | | | | 6.89 | |
| EtOH | | 5.45 | 34.8 | | 9.78 | 8.13 29.6 | 12.9 |
| MeOAc | | .33 | 2.59 | | 1.80 | .24 2.06 | 2.01 |
| other oxygenates | | .96 | 3.49 | | .88 | 1.29 1.93 | .75 |
| $H_2O$ | | 22.6 | 1.95 | | 76.7 | 32.9 1.76 | 95.8 |

*Distribution excluding $CO_2$ and $Me_2O$
[a]Reduced with hydrogen at 250° C. prior to run
[b]1 weight percent pyridine in MeOH feed immediately following run 9

The data in Table 1 demonstrates the excellent results obtained when employing the heterocyclic amine prothe number of micromoles of product formed per gram of catalyst per minute. The ethanol turnover number ranged from approximately 9.6 μmoles/g.-min. (Run No. 7) to 34.8 μmoles/g.-min. (Run No. 9) with the amine promoter catalyst. The ethanol turnover numbers without the amine promoter never exceeded approximately 8 μmoles/g.-min. (Run No. 11).

We claim:

1. A process for selectively producing ethanol which comprises reacting methanol with carbon monoxide and hydrogen in the presence of a heterogenous catalyst comprising rhodium and iron in the reduced state deposited on a support of alumina impregnated with a promoter amount of a heterocyclic amine at reaction conditions correlated so as to favor the formation of a substantial proportion of ethanol.

2. The process of claim 1 wherein said reaction conditions include a temperature within the range of from about 225° C. to about 275° C., a pressure within the range of from about 50 psig to about 250 psig, a space velocity of from about 800 to about 2000 GHSV and a mole ratio of hydrogen to carbon monoxide to methanol of about 1:1:1.

3. The process of claim 1 wherein said heterocyclic amine is selected from pyridine, isoquinoline and substituted pyridines wherein the substituents are selected from $C_1$-$C_6$ hydrocarbon alkyl.

4. The process of claim 3 wherein said heterocyclic amine is pyridine.

5. The process of claim 1 wherein said support is selected from the group consisting of alpha alumina, gamma alumina and eta alumina.

6. The process of claim 1 wherein said catalyst contains from about 1.0 to about 10.0 weight percent rhodium; from about 1.0 to about 10.0 weight percent iron and from about 0.1 to about 10.0 weight percent pyridine based on the total weight of the catalyst.

* * * * *